United States Patent [19]
Davis

[11] Patent Number: 5,174,995
[45] Date of Patent: Dec. 29, 1992

[54] TOPICAL DRUG RELEASE SYSTEM

[75] Inventor: Adrian F. Davis, Weybridge, England

[73] Assignee: Beecham Group p.l.c., England

[21] Appl. No.: 130,892

[22] Filed: Dec. 10, 1987

[30] Foreign Application Priority Data

Dec. 11, 1986 [GB] United Kingdom ................ 8629640

[51] Int. Cl.⁵ ............................................... A61R 7/06
[52] U.S. Cl. ........................................ 424/400; 424/70
[58] Field of Search ................................. 424/443, 70; 252/DIG. 13

[56] References Cited

U.S. PATENT DOCUMENTS

| | | | |
|---|---|---|---|
| 4,070,452 | 1/1978 | Bochorst | 252/DIG. 13 |
| 4,289,764 | 9/1981 | Yarrow et al. | 514/179 |
| 4,383,986 | 5/1983 | Dubash et al. | 424/443 |
| 4,722,837 | 2/1988 | Cameron | 424/70 |
| 4,767,751 | 8/1988 | Davis | 514/179 |

OTHER PUBLICATIONS

Coldman et al, J. Pharm. Sci, 58 (1969) pp. 1098–1102.

Primary Examiner—Thurman K. Page
Assistant Examiner—Leon R. Horne
Attorney, Agent, or Firm—Rosenman & Colin

[57] ABSTRACT

A topical composition containing a dissolved drug or the like (e.g. hydrocortisone acetate) preferably in saturated solution, and a solubilizer (e.g. propylene glycol), and preferably water and an antinucleant, is applied to a water-wetted area of the body, such as the hair or scalp, such that, on mixing with the body water, the resultant drug concentration exceeds the saturated drug solubility in the initially formed resultant mixture, thus giving a supersaturated drug composition.

15 Claims, 1 Drawing Sheet

TOPICAL DRUG RELEASE SYSTEM

The present invention relates to a composition method, and in particular to a composition and method for topical treatment of the human or animal body.

Hitherto, high levels of an active material (hereinafter referred to as 'the drug'), such as a pharmaceutically active material, have often been incorporated into a liquid carrier by forming a saturated solution of the drug in the carrier, thereby providing an effective topical treatment composition.

It has also been proposed (*J. Pharm. Sci.*, 58, No. 9 (1969) pp 1098-1102; Coldman et al) to create a supersaturated solution of the drug from a subsaturated solution of the drug in a mixture of a volatile and a non-volatile solvent. On topical application of the solution, the volatile solvent rapidly evaporates, thereby increasing the drug concentration to a supersaturated level. This has been found to increase the rate of drug penetration into the skin.

European published Patent Application No. 0 132 674 discloses that improved drug penetration can be obtained by creating a supersaturated drug solution using a two-phase composition mixed in situ without the need for volatile solvent evaporation.

It has now been found that a supersaturated drug system can also be created in situ by applying certain drug compositions to water-wetted areas of the body, thereby avoiding the two-phase approach of the above-mentioned European Patent Application.

According to the present invention there is provided a method for forming a supersaturated drug composition in situ for topical treatment of a human or animal body, which comprises applying a composition containing the dissolved drug (as herein defined) to a water-wetted area of the body, the composition comprising a solubilizer and sufficient dissolved drug such that, on mixing with the water on the body, the resultant drug concentration is greater than the saturated drug solubility in the initially formed resultant mixture.

The term 'drug' as used herein includes not only pharmaceutically active substances, but also, for example, other substances having a therapeutic or other beneficial effect and also cosmetic and like substances.

Preferably, the supersaturated drug composition is formed on wetted hair, as a scalp treatment method.

It has been found beneficial to retain the supersaturated composition on the water-wetted area of the body for as long as possible before being washed off, suitably from 15 to 30 minutes.

The stability of the supersaturated state is an important factor in the topical treatment, and it has been found advantageous to incorporate a soluble antinucleating agent in the drug composition to help preserve this stability.

Accordingly, in a further aspect of the invention there is provided a drug composition suitable for forming a supersaturated composition in situ when applied to a water-wetted area of a human or animal body, comprising a drug dissolved in a carrier system which contains from 0.01 to 1.0% by weight, preferably from 0.1 to 0.5% by weight of an antinucleating agent, based on the total weight of the composition, the carrier system comprising from 0 to 50% by weight of water and from 50 to 100% by weight of a solubilizer, based on the total weight of the carrier system.

Examples of suitable anti-nucleating agents are hydroxy alkylcelluloses, such as hydroxypropylmethylcellulose and hydroxypropylcellulose, polyvinylpyrrolidone, and polyacrylic acid.

The choice of a suitable anti-nucleating agent will depend both on the particular drug and the particular carrier system being used, but suitable anti-nucleating agents can readily be chosen by simple experiment. This may be done, for example, by preparing samples of the desired final supersaturated drug solution; adding a selection of anti-nucleating agents (in, say, 1% concentration), one to each sample; allowing the samples to stand for, say, 2 hours; and noting which solutions have remained clear, and thus stable. If desired, following such initial screening, further standard analytical techniques may be used to quantify the effects of selected anti-nucleating agents.

The carrier system used for dissolving the drug in the initial drug composition will generally comprise a mixture of water and a solubilizer, but it may comprise one or more solubilizers alone.

Examples of solubilizers suitable for use in the composition and method of the invention are propylene glycol, 1,3-propylene diol, polyethylene glycol, ethanol, propanol, glycerine, dimethyl sulphoxide, dimethyl acetamide, dimethyl formamide, hexylene glycol, and propylene carbonate.

It has been found advantageous to formulate the composition so that the drug is initially saturated in the composition. The degree of supersaturation, and hence rate of drug release, of the final mixture formed on the body can then be estimated from the saturated drug solubility curve for the particular solubilizer/water system.

The degree of improvement in drug penetration rate in situ will depend largely on the ratio of supersaturated drug concentration to saturated drug concentration. A ratio of greater than 1:1 is considered useful and ratios of from 2:1, for relatively slow penetration, to 10:1, for rapid penetration, are preferred. By means of the present invention, extremely high degrees of supersaturation can be obtained, and ratios of 50:1 or greater are achievable. Due to the inefficiency of percutaneous absorption, such highly supersaturated systems are of great benefit.

The drug composition of the invention may be thickened with a suitable thickening or gelling agent of either natural or synthetic origin. Examples of thickening and gelling agents are natural gums, tragacanth, carrageen, pectin, agar, alginic acid, cellulose ethers and esters, xanthan gum, guar and locust bean gum, bentonite (a colloidal hydrated aluminium silicate), veegum (colloidal magnesium aluminium silicate), laponite (a synthetic hectorite), polyvinyl alcohol, Aerosil (a trademark, colloidal silica), and Carbopol (a trademark).

The composition is preferably applied topically in a conventional manner by, for example, rubbing the composition onto the body area to be treated and leaving it for a specified period before washing away. When the composition is intended for treating the scalp, it can be applied to the hair in a similar fashion as conventional hair conditioners, although it should advantageously be left for up to 30 minutes before washing off, the exact length of time largely depending on the nature and severity of the scalp disorder.

Compositions according to the invention may also be used, for example, as toothpastes and mouthwashes, in which case the additional water is provided by saliva.

Suitable drugs for use in the composition and method of the invention are many and varied, and include the following types, with specific examples of each in brackets: steriod (hydrocortisone); anti-bacterial (tetracycline); anti-septic (chlorhexidine); anti-fungal (econazole); anti-psoriasis (dithranol); anti-acne (retinoic acid); anti-dandruff (zinc omadine); treatment of head-lice (acaricide); anti-histamine (mepyramine); local anaesthetic (benzocaine or lignocaine); analgesic, anti-inflammatory (ibuprofen); and anti-plaque (triclosan).

the respective water-wetted body site (for example, in the case of a scalp-treatment composition, the average estimated water content of the wetted hair), the resulting diluted composition will correspond to the peak plateau region of the saturation curve. Variations in the actual water content of the wetted body site will then result in only relatively small variations in the actual degree of saturation achieved (i.e. either side of the peak) with corresponding only small variations in the degree of drug penetration achieved.

TABLE 1

| FORMULATION | PARTS OF EACH SOLUTION MIXED | | RESULTANT CONCENTRATION % w/w | RESULTANT DEGREE OF SATURATION (SATURATED = 1) |
| --- | --- | --- | --- | --- |
| | HYDROCORTISONE ACETATE 0.08% w/w IN 90:10 PROPYLENE GLYCOL:WATER | WATER | | |
| A | 1 | 0 | 0.080 | 0.9 |
| B | 2 | 1 | 0.053 | 2.0 |
| C | 1 | 1 | 0.040 | 4.0 |
| D | 1 | 2 | 0.027 | 6.8 |
| E | 1 | 3 | 0.020 | 8.0 |
| F | 1 | 4.3 | 0.015 | 8.4 |
| G | 1 | 7 | 0.010 | 7.0 |
| H | 1 | 15 | 0.005 | 4.0 |

BRIEF DESCRIPTION OF DRAWING

The following examples illustrate the invention, with reference to FIG. 1, which is a graph showing solubility data of hydrocortisone acetate in water/propylene glycol mixtures, as more fully described in Example 1.

EXAMPLE 1

Formation of Supersaturated Solutions

Figure 1:
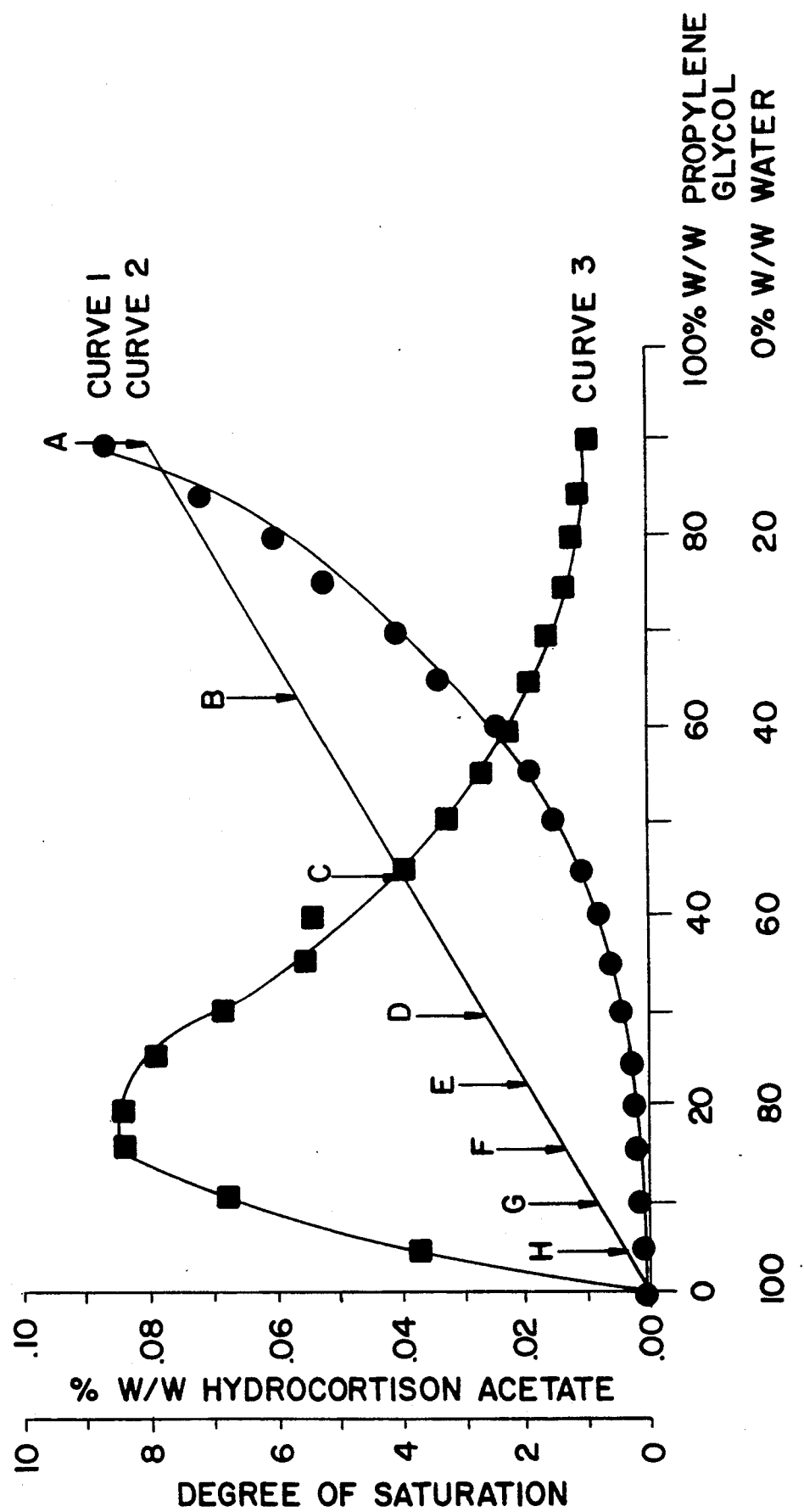

The saturation solubility of hydrocortisone acetate in mixtures of water and propylene glycol (varying from 100% water, through 50% water 50% propylene glycol, to 100% propylene glycol, in 5% steps (all percentages being weight/weight)) was determined and plotted to give the curve shown by round dots (Curve 1) in FIG. 1.

A solution of 0.08% hydrocortisone acetate in a mixture of 90% propylene glycol and 10% water was prepared (Formulation A). This was then mixed with various proportions of water, as indicated in Table 1 below, to give supersaturated Formulations B to H as plotted on the straight line (Curve 2) in FIG. 1. The resulting supersaturated concentration of hydrocortisone acetate in the diluted propylene glycol/water mixture is shown by Curve 2 and is given in Table 1.

The degree of supersaturation is determined by dividing the points on Curve 2 (at 5% intervals) with the corresponding saturation solubility on Curve 1 for the same water/propylene glycol mixture, to give Curve 3 (square dots) in which the Degree of Saturation obtained by diluting Formulation A is plotted against the resulting propylene glycol/water proportions.

It can be seen that, for a given initial drug composition (such as Formulation A), the addition of increasing amounts of water first increases the degree of supersaturation (Formulations B to D) until a plateau region is reached (Formulation E and F), whereafter the degree of supersaturation decreases again (Formulations G and H).

The drug content and carrier system water/solubiliser ratio of the drug compositions according to the present invention are advantageously so chosen that, on admixture with the average estimated water content of

EXAMPLE 2

Scalp-Treatment Formulation

A scalp-treatment formulation having the following gel composition was prepared:

| | |
| --- | --- |
| Hydrocortisone acetate | 0.08% |
| Propylene glycol | 88.58% |
| Water | 8.84% |
| Carbopol 940 | 0.5% |
| Di-isopropanolamine | 1.0% |
| Polyvinylpyrrolidone K-30 | 1.0% |

The formulation was prepared by dissolving the hydrocortisone acetate in the propylene glycol, mixing the Carbopol 940 with the hydrocortisone/propylene glycol mixture thus obtained, adding water thereto, and finally adding di-isopropanolamine and polyvinyl pyrrolidone.

The composition can be applied to wetted hair in a sufficient amount to give an overall coating and should be rubbed well in with the finger tips. The gel is left on the hair for 15 to 30 minutes and then washed off thoroughly and the hair dried.

The composition corresponds approximately to Formulation A in Example 1 and, on admixture with the water content of the wetted hair, will give formulations as indicated by Curve 2 in FIG. 1 (depending on the water content of the hair), with corresponding degrees of supersaturation as shown by Curve 3.

I claim:

1. A method for forming a supersaturated drug composition in situ for topical treatment of a human or animal body, which comprises applying to a water-wetted area of the body a composition comprising a carrier system that comprises a solubilizer and a drug dissolved in said carrier system, the amount of the dissolved drug being such that, on mixing of the composition with water on the water-wetted area of the body, the resultant drug concentration in the initially formed resultant mixture is greater than the saturated drug solubility in said resultant mixture, whereby said resultant mixture is supersaturated with the drug.

2. A method according to claim 1, wherein said carrier system contains from 0.01 to 1.0% by weight of an antinucleating agent, based on the total weight of the composition, said carrier system comprising from 0 to 50% by weight of water and from 50 to 100% by weight of said solubilizer, based on the total weight of said carrier system.

3. A method according to claim 2, wherein said carrier system contains from 0.1 to 0.5% of said antinucleating agent.

4. A method according to claim 2, wherein said antinucleating agent is a hydroxyalkylcellulose, polyvinylpyrrolidone, or polyacrylic acid.

5. A method according to claim 1, wherein said solubilizer is propylene glycol, 1,3-propylene diol, polyethylene glycol, ethanol, propanol, glycerine, dimethyl sulphoxide, dimethyl acetamide, dimethyl formamide, hexylene glycol, or propylene carbonate.

6. A method according to claim 1, wherein said applied composition is saturated with respect to said drug.

7. A method according to claim 1, wherein said composition additionally comprises a thickening or gelling agent.

8. A method as claimed in claim 1, wherein said water-wetted area of the body is the hair or scalp.

9. A drug composition suitable for forming a supersaturated composition in situ when applied to a water-wetted area of a human or animal body, comprising a drug dissolved in a carrier system which contains from 0.01 to 1.0% by weight of an antinucleating agent, based on the total weight of the composition, the carrier system comprising from 0 to 50% by weight of water and from 50 to 100% by weight of a solubilizer, based on the total weight of the carrier system.

10. A composition according to claim 9, wherein said carrier system contains from 0.1 to 0.5% of said antinucleating agent.

11. A composition according to claim 10, wherein said antinucleating agent is a hydroxyalkylcellulose, polyvinylpyrrolidone, or polyacrylic acid.

12. A composition according to claim 9, wherein said solubilizer is propylene glycol, 1,3-propylene diol, polyethylene glycol, ethanol, propanol, glycerine, dimethyl sulphoxide, dimethyl acetamide, dimethyl formamide, hexylene glycol, or propylene carbonate.

13. A composition according to claim 9, wherein the applied composition is saturated with respect to the drug.

14. A composition according to claim 9, wherein said composition additionally comprises a thickening or gelling agent.

15. A method for forming a supersaturated drug composition in situ for topical treatment of a human or animal body, which comprises applying to a water-wetted area of the body a composition comprising a carrier system that comprises a solubilizer and a drug dissolved in said carrier system, said carrier system comprising from 0 to 50% by weight of water and from 50 to 100% by weight of said solubilizer, based on the total weight of said carrier system, and the amount of the dissolved drug being such that, on mixing of the composition with water on the water-wetted area of the body, the resultant drug concentration in the initially formed resultant mixture is grater than the saturated drug solubility in said resultant mixture, whereby said resultant mixture is supersaturated with the drug.

* * * * *